United States Patent [19]
Rall et al.

[11] Patent Number: 5,865,737
[45] Date of Patent: Feb. 2, 1999

[54] SENSOR DEVICE FOR MEASURING THE VITAL PARAMETERS OF A FETUS DURING BIRTH

[76] Inventors: Gerhard Rall, Bozzaristrasse 39f, D-81545 München; Reinhold Knitza, Bergstrasse 46a, D-82152 Krailling, both of Germany

[21] Appl. No.: 793,079
[22] PCT Filed: Aug. 4, 1995
[86] PCT No.: PCT/EP95/03118
§ 371 Date: Jul. 17, 1997
§ 102(e) Date: Jul. 17, 1997
[87] PCT Pub. No.: WO96/04843
PCT Pub. Date: Feb. 22, 1996

[30] Foreign Application Priority Data

Aug. 7, 1997 [DE] Germany .......................... 44 27 864.0

[51] Int. Cl.⁶ ...................................................... A61B 5/00
[52] U.S. Cl. .......................... 600/338; 600/351; 600/376; 600/511
[58] Field of Search ..................................... 600/313, 338, 600/342, 351, 376, 511, 333

[56] References Cited

U.S. PATENT DOCUMENTS

| | | |
|---|---|---|
| 4,658,825 | 4/1987 | Hochberg et al. ...................... 600/313 |
| 4,913,151 | 4/1990 | Harui et al. . |
| 5,154,175 | 10/1992 | Gunther .................................. 600/333 |

FOREIGN PATENT DOCUMENTS

| | | |
|---|---|---|
| 0 104 619 | 4/1984 | European Pat. Off. . |
| 2619471 A1 | 11/1977 | Germany . |
| 27 49 048 | 3/1979 | Germany . |
| 381008 C1 | 10/1989 | Germany . |

Primary Examiner—Robert L. Nasser
Assistant Examiner—Eric F. Winakur
Attorney, Agent, or Firm—Burns, Doane, Swecker & Mathis, L.L.P.

[57] ABSTRACT

A sensor device for measuring the vital parameters of a fetus during birth. The sensor device includes a sensor having a wire spiral for attaching the sensor to the fetus, and a placement device for placing the sensor on a leading part of the fetus. A measuring device is connected to the sensor, and the sensor has on a front side facing the fetus at least one light emitter and at least one receiver which are conductively connected with the measuring device. The conductors are arranged in a cable branching off the sensor towards the measuring device, and the cable is introduced laterally, and essentially tangentially, onto a back surface of the sensor and extending in front of an insertion point into the sensor to form a helical partial winding approximately in a plane that extends approximately perpendicular to a center axis of the wire spiral. This arrangement is advantageous in that the cable does not interfere with the tight contact of the sensor with the tissue of the fetus, either during the placement of the sensor or during birth, ensuring that reliable signals will always be received from the fetus during the entire duration of the birth.

19 Claims, 4 Drawing Sheets

SENSOR DEVICE FOR MEASURING THE VITAL PARAMETERS OF A FETUS DURING BIRTH

BACKGROUND OF THE INVENTION

1. Field of the Invention

The invention relates to a sensor device for measuring the vital parameters of a fetus during birth.

2. Field of the Invention

A sensor device for measuring the vital parameters of a fetus is known, for example, from German patent DE 38 100 08. Such a sensor device includes a sensor, a placement device for placing the sensor on the leading part of the fetus, and a measuring device connected to the sensor, whereby the sensor has on its front side facing the fetus and, arranged in the center of the sensor, a wire spiral for attaching the sensor to the fetus, and at least one light emitter and at least one receiver which are connected by way of conductors with the measuring device, said conductors arranged in a cable branching off the sensor towards the measuring device.

In this known sensor, the cable exits the sensor through the back of the sensor on the opposite side of the wire spiral, approximately in the direction of the main axis of the wire spiral.

Praxis has shown that usable signals can be received reliably only when the sensor is in tight contact with the tissue of the fetus for the duration of the birth. But during birth, a rotation of the fetal head frequently causes the sensor to move below the cervix.

In the process, the cable is bent and thus exerts a tilting moment on the sensor, possibly having an adverse effect on its attachment to the fetus. This risk is increased if in addition a pull is exerted on the sensor via the cable. Actually, such a risk already exists during the placement of the sensor.

SUMMARY OF THE INVENTION

The present invention is based on the task of constructing a sensor device of the above mentioned type in such way a that the functions of the sensor are safely attained during its placement and are safely maintained during birth, regardless of any relative movements between the fetus and the mother.

In order to realize this objective, the invention provides that in such a sensor device the cable is introduced laterally, and essentially tangentially, into the back of the sensor and extends in front of the insertion in a helical partial winding, e.g., in a plane that extends more or less vertically to the axis of the wire spiral.

This measure makes it possible that the cable spiral, i.e., the partial winding on the back of the sensor, is able to slip underneath the cervix in an essentially flat position together with the sensor, while no tilting moment is exerted on the sensor. Any pulling on the cable during the process, or even during the sensor placement, will not prevent the secure placement of the sensor or its reliable attachment to the fetus during birth, independent from any relative movements between mother and fetus, since the springy, resilient partial winding of the cable spiral always prevents an adverse pulling action on the sensor. In order to retain the partial winding of the cable spiral in its flat position without adversely affecting the above described advantages, the partial winding of the spiral can be held on the sensor back in an easily releasable manner, e.g., in a groove or by way of a point attachment at a clamping point with an easily releasable clip. The retention force can be kept so low that, in the case of a possible adverse pulling on the cable, the partial winding of the cable spiral is released. However, the partial winding can also be kept in its position by being constructed in a resilient rigid construction.

This may also be an additional measure.

In order to attain a reliable attachment of the sensor device on the fetus during its placement, the placement device of the sensor device may, in a known manner, have a guide tube with a screwdriver for rotating the sensor guided inside it, whereby the cable coming from the sensor is guided through the guide tube, but whereby this placement device according to the invention can be further developed in such a way that the front end of the guide tube has a chalice-like receptacle that holds both the sensor and the partial winding, whereby the cable part adjoining the partial winding is held in a position that will follow along with the rotation of the screwdriver.

In this way, the partial winding is also secured in its position during the placement while preventing the cable part inside the guide tube from exerting a harmful pull on the sensor during the rotating of the sensor with the screwdriver.

This may be achieved, e.g., in such a way that the cable is held behind the partial winding in a longitudinal groove of the screwdriver.

BRIEF DESCRIPTION OF THE DRAWINGS

The invention will be described in greater detail with reference to the accompanying drawings wherein a preferred embodiment of the present invention is illustrated, and wherein.

DESCRIPTION OF THE PREFERRED EMBODIMENT

Figure 1:
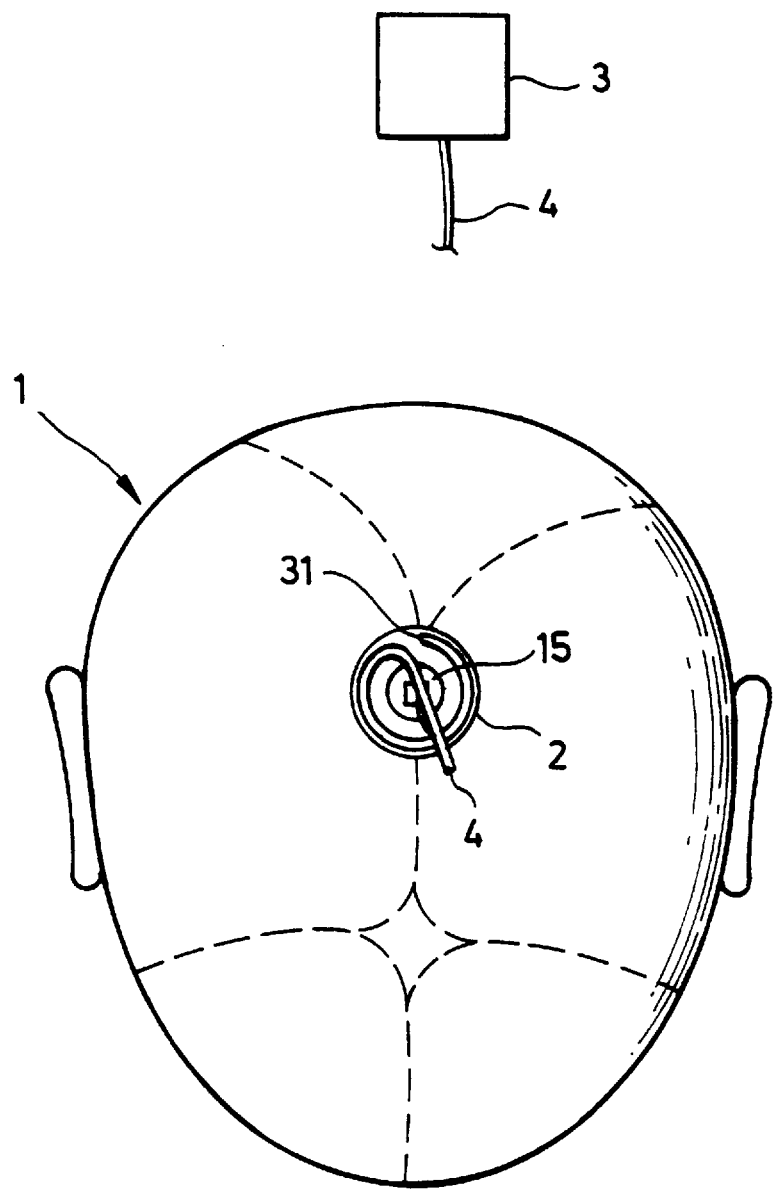
FIG. 1 shows a view from the top onto the sensor attached to the head of the fetus, approximately on a natural scale.
Figure 2:
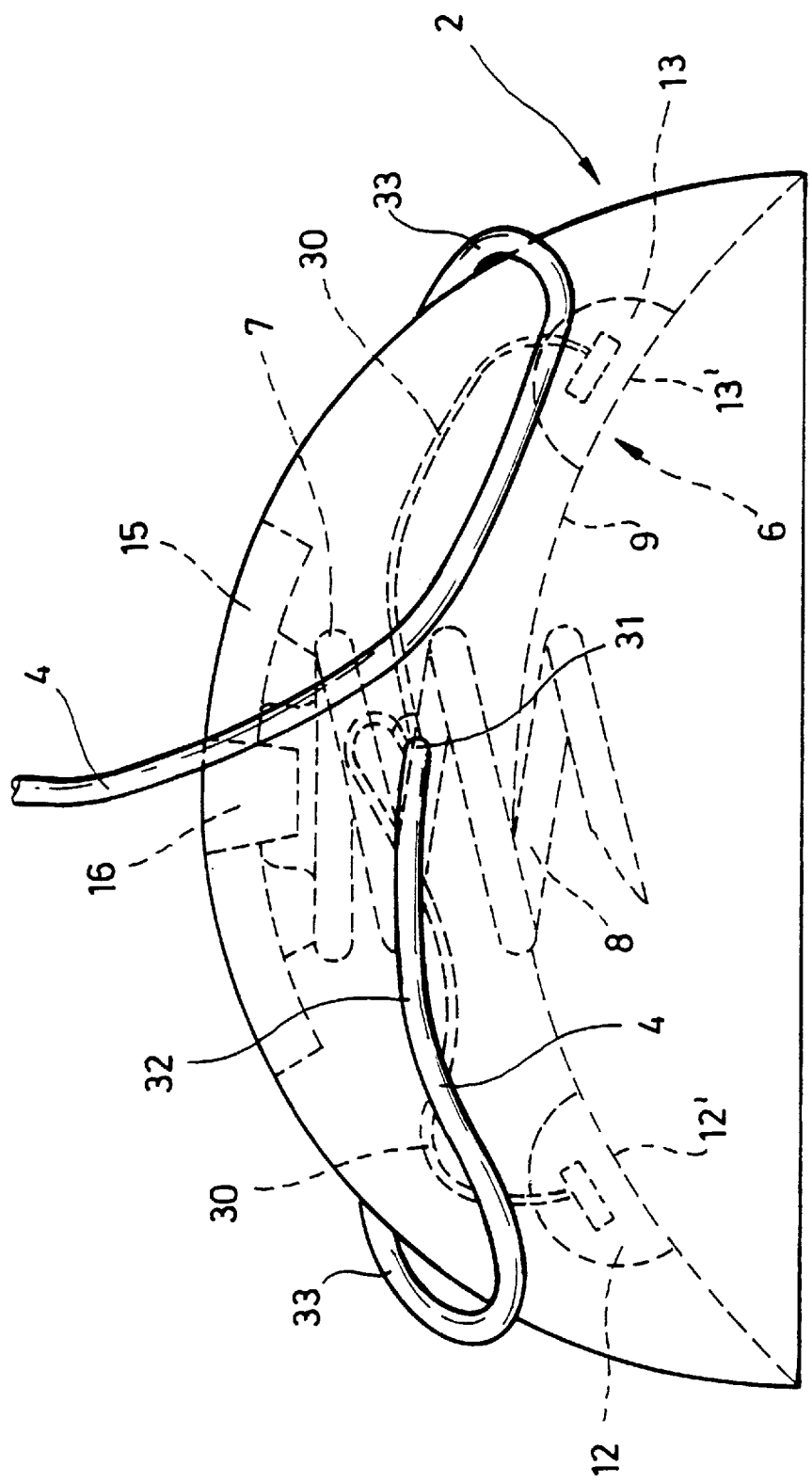
FIG. 2 shows a lateral view of the sensor, on a greatly enlarged scale.

FIG. 1 shows a top view of the head 1 of the fetus, whereby the mother's birth canal is not shown for better clarity of the drawing. The sensor 2 is inserted through the vagina and attached to the head 1. Seen from the top, it has an approximately circular shape. Its lateral view, in FIG. 2, shows that the sensor 2, which consists of an elastic material, is bowl-shaped, a fact that is particularly advantageous in connection with the invention. A cavity 6 is located on the front side facing the fetus. In the center of the bowl, a wire spiral 7 is imbedded and projects with approximately one winding 8 from the surface 9 of the cavity 6.

A light emitter 12 and a receptacle 13 are imbedded in the material of the sensor 2 in such a way that their surface 12' and 13' extends approximately flush with the surface 9 of the cavity 6.

The sensor 2 is provided on its back, i.e., on its convex side, with a metal plate 15 that is partially imbedded in the material of the sensor 2 and is tightly connected there to the wire spiral 7, whereby the wire spiral and metal plate are electrically insulated from each other. The metal plate 15 forms one unit with a polygonal socket 16 located in the center, e.g., a square socket serving as a coupling part for a rotating placement device in the form of a socket pin drive that can be released from the sensor.

The light emitter 12 and the receiver 13 are each connected with a conductor 30 to the measuring device 3.

These conductors 30 are guided inside a cable 4 that is inserted laterally and essentially tangentially into the back of the sensor 2 and which runs inside a spiral prior to the introduction point 31. It has a partial winding 33 extending essentially flat while lying closely above or on the sensor 2. The partial winding 33 changes into a part that extends away from the sensor 2 at an angle and then extends approximately straight, preferably up to the measuring device 3.

Figure 4:
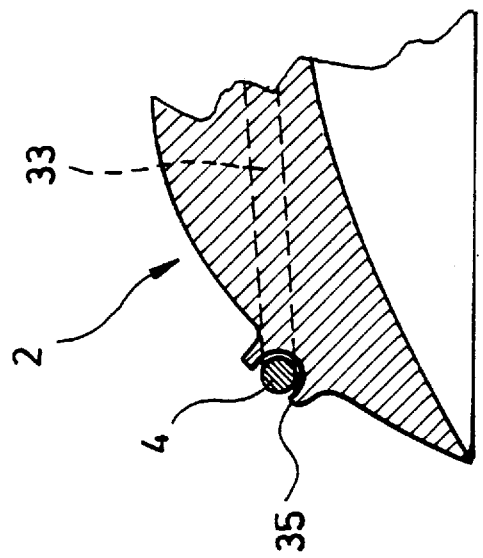
FIG. 3 and 4 show details about the loose retention of the partial winding of the cable spiral on the sensor back; and, FIG. 5 shows a partial section of the arrangement of sensor, partial winding and adjoining cable part in the placement device.
Figure 3:
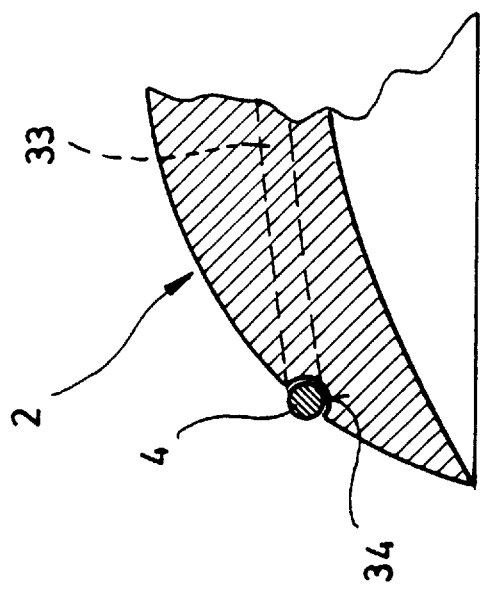

The partial winding 33 is able to retain its flat shape closely above or on the back of the sensor 2 because the material of the cable 4 has an appropriate resilient rigidity. However, it is also possible to keep the partial winding 33 in place by inserting it into a clamping groove 34 which is worked into the back of the sensor 2. (FIG. 3) Another possibility is shown in FIG. 4, where the partial winding 33 is held at one point, at a distance from the insertion point of the cable into the sensor 2, in a clamping point 35 that clips while providing a small amount of give. Sometimes medical reasons require that the sensor must be removed from the fetal head during birth.

In the past, this has been difficult, since a central introduction of the cable does not permit this, and a grasping of the sensor which is covered with birth fluid is also practically impossible.

The lateral introduction of the cable into the sensor makes it possible, however, to place one finger through the lateral introduction point of the cable to exert a turning moment on the sensor in order to detach it.

Figure 5:
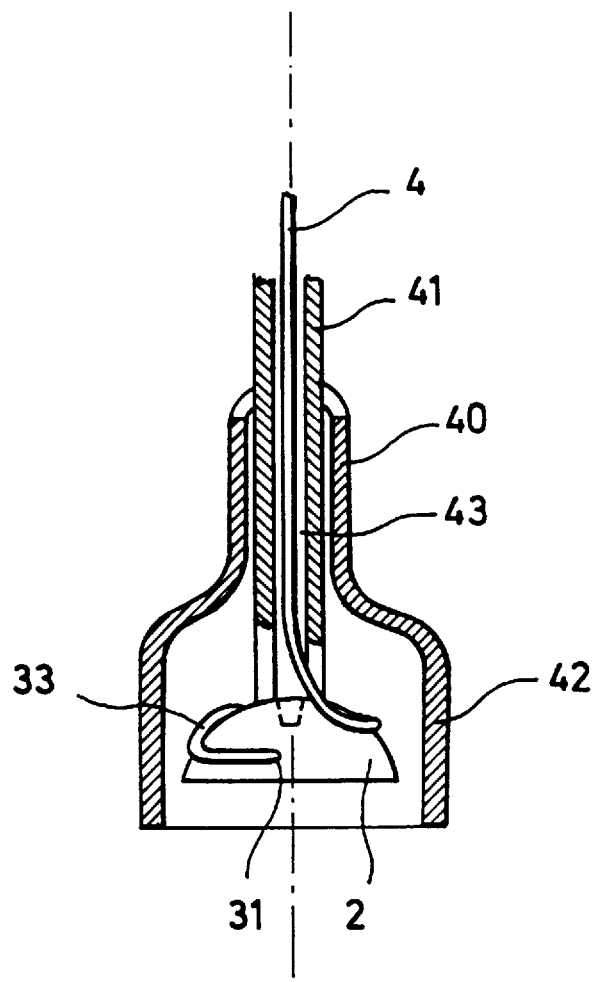

FIG. 5 shows a partial section of the placement device, i.e., a guide tube 40 with an approximately circular cross-section and a screwdriver 41 guided in it in a rotatable and movable manner, said screwdriver being inserted with a square into the square socket 16 of the sensor 2. The guide tube 40 has at its front end a chalice-like receptacle 42 in which the sensor 2 is located, whereby the partial winding 33 is also inside the receptacle 42. The screwdriver 41 has a longitudinal groove 43 holding that part of the cable 4 that adjoins the partial winding 33.

When placing the sensor, the assembled placement device is inserted through the vagina in such a way that the chalice-like receptacle 42 sits on the head of the fetus. The sensor 2 is then moved forward with the screwdriver 41 until the sensor 2 rests against the head of the fetus.

The sensor 2 is now turned with the screwdriver 41 so that the wire spiral 7 turns into the scalp of the fetus and holds the sensor 2 tightly to the tissue of the fetus. The cable 4 that is located in the groove 43 of the screwdriver 41 rotates along with the screwdriver 41 so that the partial winding 33 thereby maintains its position at or closely above the sensor 2. No pull is exerted on the partial winding 33. Such a pull would create a risk of tilting and pulling out of the wire spiral from the tissue of the fetus.

After the sensor is attached in this manner to the head of the fetus, the guide tube 40 and the screwdriver can be retracted from the vagina, whereby the cable 4 is removed from the groove 43. The sensor 2 remains anchored to the head of the fetus by way of the wire spiral 7; the partial winding 33 maintains its flat position at or closely above the sensor 2.

The lateral, spiral-shaped introduction of the cable (4) into the sensor can be used both for curved, bowl-shaped sensors as well as for other shapes, such as, e.g., a cylindrically shaped sensor or a flattened, rotation-symmetrical sensor, as it is known from DE-26 19 471. With it, mechanical forces that are transferred from the cable (4) onto the sensor (2) can be minimized, resulting in a good ratio of signal to noise influences. The forces that must be absorbed by the cable (4) itself also are minimized.

The lateral insertion of the cable (4) into the sensor (2) prevents overbending of the cable (4) if the sensor should slip under the cervix. Axial cable introducers would be greatly bent in this eventuality.

The spiral shape of the cable (4) in addition represents a certain reserve in the length of the cable, so that in the case that the cable (4) is slightly pulled, the cable (4) is not tightened. The spiral shape also makes the cable (4) more flexible overall, so that the cable material itself can be constructed somewhat more flexibly while retaining the high flexibility of the cable shape.

These advantages are particularly important when fiber optical waveguides are used. Fiber optical waveguides are known as relatively susceptible to bending and tangling. Tight bending radii may result in light losses and have the inherent risk that the optical fiber will break. On the other hand, optical fibers facilitate the use of spectroscopic analyses that are able to measure and transmit a number of medical parameters.

The cable introduction according to the invention also can be used for sensors with fiber optical waveguides in the wire spiral. The waveguides hereby can be guided in the winding cannula (wire spiral) with an advantageous curve that has an appropriate curvature. It is, e.g., possible that a conductor for one of the optical elements (emitter or receiver) is introduced into the wire spiral, and the optical element is able to exit at the tip or at other points from the wire spiral, whereby the other optical element is provided in the rim area or centrally in the bowl.

We claim:

1. Sensor device for measuring the vital parameters of a fetus during birth, said device comprising: a sensor having a wire spiral for attaching the sensor to the fetus, the sensor including a front side adapted to face the fetus, a placement device for placing the sensor on a leading part of the fetus, a measuring device connected to the sensor, the sensor having on its front side at least one light emitter and at least one receiver which are connected by way of conductors with the measuring device, said conductors being arranged in a cable branching off the sensor towards the measuring device, the cable approaching laterally, and substantially tangentially, onto a back surface of the sensor and extending in front of an insertion point into the sensor to form a helical partial winding substantially in a plane that extends substantially perpendicular to a center axis of the wire spiral.

2. Sensor device as claimed in claim 1, wherein the partial winding is held on the back surface of the sensor in a releasable manner.

3. Sensor device as claimed in claims 1 or 2, wherein the partial winding is guided in a clamping groove in the back surface of the sensor.

4. Sensor device as claimed in claims 1 or 2, wherein the partial winding is held at one point in a clamping point in the back surface of the sensor that clips the partial winding while providing a small amount of give.

5. Sensor device as claimed in claims 1 or 2, wherein the partial winding is resiliently rigid such that it maintains its position.

6. Sensor device as claimed in claim 1, wherein the placement device includes a guide tube and a screwdriver for rotating the sensor guided in the guide tube, whereby a portion of the cable extending from the sensor passes through the guide tube, the front end of the guide tube having a chalice-like receptacle that holds the sensor and the partial winding, a part of the cable adjoining the partial winding being held in a position such that it will rotate with the screwdriver when the screwdriver is rotated.

7. Sensor device as claimed in claim 6, wherein the cable is held behind the partial winding in a longitudinal groove in the screwdriver.

8. A sensor device for measuring a vital parameter of a fetus during birth, the sensor device comprising:

a sensor having an exterior surface and a detecting device for detecting the vital parameter of the fetus;

a cable in electrical communication with the detecting device, said cable tangentially approaching an exterior surface of said sensor and helically winding at least 180° about said exterior surface as measured from an introduction opening into an interior of said sensor to define a helically winding portion of said cable, said helically winding portion lying substantially in a plane.

9. The sensor device as claimed in claim 8, wherein an introduction portion of said cable is located relative to said exterior surface so as to laterally approach said exterior surface at an acute angle with respect to said plane prior to tangentially approaching said exterior surface.

10. The sensor device as claimed in claim 9, wherein said cable helically winds substantially 360° about said surface as measured from said introduction opening to said introduction portion of said cable.

11. The sensor device as claimed in claim 8, wherein said helically winding portion of said cable is releasably attached to said exterior surface of said sensor.

12. The sensor device as claimed in claim 8, wherein said exterior surface includes a groove for receiving said helically winding portion of said cable.

13. The sensor device as claimed in claim 8, wherein said sensor includes a wire spiral for attaching said sensor to the fetus, said cable helically winding such that said helically winding portion of said cable is substantially perpendicular to a center axis of said wire spiral.

14. The sensor device as claimed in claim 8, wherein said exterior surface is circular.

15. The sensor device as claimed in claim 8, wherein said cable is resilient.

16. The sensor device as claimed in claim 8, wherein said detecting device includes at least one light emitter and at least one receiver.

17. The sensor device as claimed in claim 8, wherein said helically winding portion of said cable is adjacent to said exterior surface but not touching said exterior surface.

18. The sensor device as claim in claim 8, in combination with a placement device, said placement device having a receptacle holding said sensor and said cable, said placement device including a guide tube attached to said sensor and receiving a portion of said cable.

19. A sensor device for measuring a vital parameter of a fetus during birth, the sensor device comprising:

a sensor having an exterior surface and means for detecting the vital parameter of the fetus;

means for attaching said sensor to the fetus;

a cable in electrical communication with said means for detecting, said cable being located and configured relative to said exterior surface so as to permit a helical winding portion of said cable immediately adjacent to said sensor to slip underneath a cervix in a substantially flat position together with said sensor when the sensor is attached to the fetus and the fetus moves.

* * * * *